United States Patent
Viders

(10) Patent No.: US 6,228,351 B1
(45) Date of Patent: May 8, 2001

(54) MEDICATED LIP BALM

(76) Inventor: Daniel E. Viders, 28 Lynwood La., West Boylston, MA (US) 01583

(*) Notice: Subject to any disclaimer, the term of this patent is extended or adjusted under 35 U.S.C. 154(b) by 0 days.

(21) Appl. No.: 09/503,997

(22) Filed: Feb. 14, 2000

Related U.S. Application Data

(60) Provisional application No. 60/136,255, filed on May 27, 1999.

(51) Int. Cl.⁷ .................. A61K 7/025; A61K 47/00
(52) U.S. Cl. .............................. 424/64; 514/787
(58) Field of Search .................. 424/358, 59, 64; 514/787

(56) References Cited

U.S. PATENT DOCUMENTS

| | | |
|---|---|---|
| 4,303,639 | 12/1981 | Vanlerberghe et al. . |
| 4,346,086 | 8/1982 | Sattler et al. . |
| 4,478,853 * | 10/1984 | Chaussee .................. 424/358 |
| 4,738,956 | 4/1988 | Scott et al. . |
| 4,814,165 | 3/1989 | Berg et al. . |
| 4,902,682 | 2/1990 | Sattler et al. . |
| 4,959,205 * | 9/1990 | Brunner et al. ............... 424/59 |
| 5,023,251 | 6/1991 | Sattler et al. . |
| 5,085,856 | 2/1992 | Dunphy et al. . |
| 5,093,111 | 3/1992 | Baker et al. . |
| 5,112,816 | 5/1992 | Narui et al. . |
| 5,466,457 | 11/1995 | Schneider et al. . |

* cited by examiner

Primary Examiner—Thurman K. Page
Assistant Examiner—Blessing Fubara
(74) Attorney, Agent, or Firm—Blodgett & Blodgett, P.C.

(57) ABSTRACT

A lip balm containing from 0.2% to 2.5% hydrocortisone in a base of beeswax mineral oil and petroleum jelly. The amount of petroleum jelly is not more than that of the beeswax and mineral oil combined and the amount of mineral oil is roughly equal to the amount of beeswax.

5 Claims, No Drawings

MEDICATED LIP BALM

CROSS-REFERENCE TO RELATED APPLICATIONS

This application claims the benefit under 35 U.S.C. §119 (e) of prior U.S. Provisional application Ser. No. 60/136,255 filed May 27, 1999; all of which is hereby incorporated by reference.

STATEMENT REGARDING FEDERALLY SPONSORED RESEARCH OR DEVELOPMENT

This invention has been created without the sponsorship or funding of any federally sponsored research or development program.

BACKGROUND OF THE INVENTION

The present invention is directed to a medicated lip balm for treating cheilitis, a medical term for painful dry inflamed lips. There are many causes of cheilitis, including severe weather conditions and one of the side effects from the use of medications, such as isotretinoin, for treating severe acne.

The chief treatment for cheilitis through the use of lip balms which contain phenol, menthol or camphor. Traditional lip balms are ineffective in the treatment of cheilitis and, in many cases, make the condition worse.

Although there are suggestions in the prior art for the use of hydrocortisone as an ingredient in lip balms or sticks, the prevailing medical view is that any lip balm which contains hydrocortisone should not be used on mucous membranes. Other current treatment for cheilitis includes ointments which contain hydrocortisone as the medication and base for delivering the medication to the epidermis of the lips. Most ointments have an unpleasant taste and a base, such as thick petroleum jelly, which is not entirely suitable. A suitable base is defined as a material capable delivering a medication to the epidermis (diffuse into the epidermis) as determined by the relative solubility of the active ingredient in the base, usually called the vehicle, versus the solubility of the material in the epidermis. Since the lips have a moist surface, there is a tendency for the base not to "stick". Some lip balms have a base which includes a combination of wax and a mineral oil or a combination of wax and petroleum jelly. The mineral oil or the petroleum jelly allows the lip balm to be transferred or applied to the lips. The wax holds the medication on the lips and lets the medication diffuse into the skin. The correct ratios for the wax and petroleum jelly or wax and mineral oil are difficult or nearly impossible to obtain. The lip balm is either too stiff (due to the wax) or too greasy (due to the petroleum jelly or to the mineral oil).

These and other difficulties experienced with the prior art lip balms have been obviated by the present invention.

A principle object of the invention is the provision of a lip balm that includes hydrocortisone of a concentration that is effective in the treatment of cheilitis and is considered safe as dictated by FDA standards and a base which permits diffusion of the hydrocortisone into the epidermis of the lips and which enables the lip balm to stay on the lips for a sufficient time to permit diffusion of the hydrocortisone into the epidermis of the lips.

Another object of the invention is the provision of a lip balm which is not objectionably greasy and sufficiently rigid to be self supporting without being too stiff.

BRIEF SUMMARY OF THE INVENTION

A lip balm containing from 0.2% to 2.5% hydrocortisone in a base of beeswax mineral oil and petroleum jelly. The amount of petroleum jelly is not more than that of the beeswax and mineral oil combined the amount of mineral oil is preferably roughly equal to the amount of beeswax but one of these substances does not exceed the other by more than 4%.

DETAILED DESCRIPTION

The lip balm of the present invention comprises a steroid hormone, preferably hydrocortisone, as the active ingredient and a base which includes a combination of beeswax, petroleum jelly and mineral oil. The amount of hydrocortisone in the base is to some degree dependant on the condition to be treated. To be effective, the hydrocortisone must constitute at least 0.2 % of the lip balm. The upper 'safe' percentage limit of hydrocortisone, as determined by FDA standards, is 1.0% for a non prescription product and 2.5% for a prescription product.

The three ingredients of the base, beeswax, petroleum jelly, and mineral oil allow many effective base combinations to be made. Acceptable ratios of these constituents can be formulated based on the following relationships. The percentage of the wax and mineral oil are similar. A one to one ratio of wax to mineral oil is ideal. Acceptable bases are obtained by increasing either of these two ingredients relative to the other up to a point wherein one of the ingredients is 40% greater than the other.

The petroleum jelly portion of the base should be substantially equal to and preferably less than the beeswax and mineral oil combined. The effective percentage range of the petroleum jelly is between 40% and 50% of the total base of the lip balm. The ideal percentage of petroleum jelly in the base is 45%. The lip balm of the present invention is made by heating a quantity of beeswax until completely melted. It is preferred that the beeswax be melted at 62° C. or substantially less to prevent degradation or damage to the wax. The melted beeswax is added to petroleum jelly and mineral oil. This mixture is maintained above the melting point of the beeswax and stirred for several minutes. Hydrocortisone powder is then added to the above mixture. The final mixture is maintained above the melting point of the beeswax and stirred for several minutes.

The final mixture described above is poured, while still warm and fluid, into appropriate tubes and allowed to cool until solid. The resulting lip balm of the present invention is in the form of a stick. However, the lip balm of the present invention can also be marketed in a small wide mouth jar.

The following examples illustrate the lip balm of the present invention.

EXAMPLE 1

A lip balm is prepared with the specified constituents:

| | |
|---|---|
| pure hydrocortisone powder | 1.00 g |
| pure beeswax | 25.00 g |
| petroleum jelly | 49.00 g |
| mineral oil | 25.00 g |
| | 100.00 g |

EXAMPLE 2

A lip balm is prepared with the specified constituents:

| | |
|---|---:|
| pure hydrocortisone powder | .20 g |
| pure beeswax | 22.00 g |
| petroleum jelly | 49.80 g |
| mineral oil | 28.00 g |
| | 100.00 g |

EXAMPLE 3

A lip balm is prepared with the specified constituents:

| | |
|---|---:|
| pure hydrocortisone powder | 2.00 g |
| pure beeswax | 28.00 g |
| petroleum jelly | 47.00 g |
| mineral oil | 23.00 g |
| | 100.00 g |

EXAMPLE 4

A lip balm is prepared with the specified constituents:

| | |
|---|---:|
| pure hydrocortisone powder | 2.50 g |
| pure beeswax | 22.00 g |
| petroleum jelly | 45.00 g |
| mineral oil | 30.00 g |
| | 100.00 g |

EXAMPLE 5

A lip balm is prepared with the specified constituents:

| | |
|---|---:|
| pure hydrocortisone powder | 1.00 g |
| pure beeswax | 22.25 g |
| petroleum jelly | 44.50 g |
| mineral oil | 32.25 g |
| | 100.00 g |

What is claimed:

1. A lip balm comprising a mixture of 0.2% by weight up to 2.5% by weight of hydrocortisone and a base of petroleum jelly, beeswax and mineral oil, said petroleum jelly being substantially from 40% by weight to 50% by weight of said base, the amount by weight of one of said beeswax and said mineral oil being no more than 40% greater by weight than the other of said beeswax and said mineral oil, the amount of said beeswax and mineral oil together being substantially 50% by weight of said mixture.

2. A lip balm as recited in claim 1, wherein the percentage by weight of said beeswax is substantially equal to the percentage by weight of said mineral oil.

3. A lip balm as recited in claim 1, wherein said petroleum jelly is about 45% by weight of said base.

4. A method of preparing a lip balm comprising the following steps:

(a) heating a quantity of beeswax until said beeswax is melted;

(b) adding said melted beeswax to a quantity of petroleum jelly and ea oil to form a base mixture, said petroleum jelly being from 40% by weight to 50% by weight of said base mixture, the amount of one of said beeswax and said mineral being no more than 40% greater by weight of the other of said beeswax and said mineral oil and the amount of beeswax and mineral oil together being substantially 50% by weight of said base;

(c) sting said base mixture for several minutes while maintaining the temperature of said base mix e above the melting point of said beeswax;

(d) adding a quantity of hydrocortisone to said base mixture to form a final lip balm mixture, said quantity of hydrocortisone being from 0.2% by weight to 2.5% by weight of said final lip balm mixture;

(e) stirring said final lip balm mixture for several minutes while maintaining said final lip balm mixture above the melting point of said beeswax; and (f) pouring said final lip balm mixture into an appropriate receptacle.

5. A method of preparing a lip balm as recited in claim 4, wherein the temperature of said beeswax and said base mixture does not exceed 62 C.

\* \* \* \* \*